United States Patent [19]

Jarvis et al.

[11] 4,244,931
[45] Jan. 13, 1981

[54] DICALCIUM PHOSPHATE DIHYDRATE WITH IMPROVED STABILITY

[75] Inventors: William M. Jarvis, Webster Groves; Keun Y. Kim, Clayton, both of Mo.

[73] Assignee: Monsanto Company, St. Louis, Mo.

[21] Appl. No.: 43,413

[22] Filed: May 29, 1979

[51] Int. Cl.$^3$ .............. C01B 25/00; C01B 15/16; C01B 25/26

[52] U.S. Cl. ................ 423/266; 423/308; 423/311; 423/267; 424/57

[58] Field of Search ........... 423/265, 266, 267, 307, 423/308, 309, 311, 313; 424/57

[56] References Cited

U.S. PATENT DOCUMENTS

| | | | |
|---|---|---|---|
| 2,852,341 | 9/1958 | Bell et al. | 423/308 |
| 3,012,852 | 12/1961 | Nelson | 423/267 |
| 3,066,056 | 11/1962 | Schlaeger | 423/267 |
| 3,464,786 | 9/1969 | Harnisch et al. | 423/313 |

Primary Examiner—O. R. Vertiz
Assistant Examiner—Gregory A. Heller
Attorney, Agent, or Firm—S. M. Tarter; W. H. Duffey; F. D. Shearin

[57] ABSTRACT

Dicalcium phosphate dihydrate containing a sufficient amount of trimagnesium phosphate and/or tetrasodium pyrophosphate to inhibit spontaneous hydrolysis and/or decomposition of the dicalcium phosphate dihydrate is widely used as a dental polishing agent with and without added fluoride. Now it has been found that dicalcium phosphate dihydrate containing a sufficient amount of pyrophosphate to provide hydrolytic stability to the dicalcium phosphate can have improved soluble fluoride stability when at least 0.1 weight percent of trimagnesium phosphate and a pharmaceutically acceptable polyphosphate salt are each added to the formulation. In the preferred embodiment, less than 2 percent pentasodium tripolyphosphate provides satisfactory results.

9 Claims, No Drawings

DICALCIUM PHOSPHATE DIHYDRATE WITH IMPROVED STABILITY

BACKGROUND OF THE INVENTION

The present invention relates to novel dentifrice abrasives, and more particularly to dicalcium phosphate dihydrate with improved fluoride stability.

Dicalcium orthophosphate dihydrate ($CaHPO_4 \cdot 2H_2O$) that has been stabilized against spontaneous hydrolysis and/or decomposition with a small amount of tetrasodium pyrophosphate in accordance with the processes such as those described by Moss et al in U.S. Pat. No. 2,287,699 or with trimagnesium orthophosphate and the like, has been utilized in dental preparations for many years. Indeed, dicalcium phosphate dihydrate frequently is stabilized against spontaneous hydrolysis and/or decomposition with a small amount of both tetrasodium pyrophosphate and trimagnesium phosphate in dental preparations.

Furthermore, as is known to those skilled in the art, dentifrice formulations using dicalcium phosphate dihydrate frequently contain sodium monofluorophosphate as a source of fluoride ion to inhibit or retard the formation of dental caries. Thus, the use of dicalcium phosphate dihydrate with sodium monofluorophosphate and stabilized against spontaneous decomposition and/or hydrolysis with tetrasodium pyrophosphate and/or trimagnesium phosphate, either with or without other polishing agents, are well known to those skilled in the art.

Although satisfactory results are obtained using the dental formulations as set forth above, it has been found that over a period of time the soluble fluoride is lost from the dental formulations. For example, it has been found that dental formulations containing dicalcium phosphate dihydrate stabilized with tetrasodium pyrophosphate at up to 1 weight percent by weight $P_2O_5$, as pyrophosphate, or about 2 weight percent trimagnesium phosphate octahydrate, and sufficient sodium monofluorophosphate to provide about 1,000 parts per million soluble fluoride will lose a substantial amount of the soluble fluoride after prolonged storage. Only a small improvement is seen when both trimagnesium phosphate and tetrasodium pyrophosphate are used together with respect to soluble fluoride stability.

Although applicants do not wish to be bound by any particular theory, it is believed that the loss of soluble fluoride in the formulation is due to the hydrolytic instability of the dicalcium phosphate dihydrate. It is believed that fluoride ion catalyzes the formation of calcium hydroxyapatite which then reacts with the soluble fluoride to form water-insoluble calcium fluoroapatite. Hence, it can be seen that improved fluoride stability of dicalcium phosphate dihydrate would probably provide improved stability against spontaneous hydrolysis and/or decomposition.

Accordingly, it can be seen that there is a need for a composition suitable for use as a dental polishing agent containing dicalcium phosphate dihydrate with improved soluble fluoride stability which will provide greater amounts of soluble fluoride after prolonged storage. Now, an improved composition to meet these criteria is provided.

SUMMARY OF THE INVENTION

These and other advantages are achieved by a composition which comprises dicalcium phosphate and (a) at least 0.1 weight percent trimagnesium phosphate, (b) at least 0.1 weight percent $P_2O_5$ as pyrophosphate complex, and (c) at least 0.1 weight percent of a pharmaceutically acceptable polyphosphate salt.

The term "DCPD" as it is used in the specification and claims shall mean dicalcium phosphate dihydrate. The term "pyrophosphate complex" shall mean the chemical composition that is formed when a soluble pyrophosphate salt or calcium-alkali metal pyrophosphate is added to DCPD during the precipitation stage to provide conventional hydrolytic stability to the DCPD. The term "hydrolytic stability" with respect to DCPD shall mean DCPD that has been stabilized against spontaneous hydrolysis and/or decomposition.

Broadly described, the compositions of the present invention can be prepared by adding a basic calcium-containing material to dilute orthophosphoric acid and adding a sufficient amount of soluble pyrophosphate salt to form the pyrophosphate complex that provides at least partial hydrolytic stability to the DCPD. The DCPD is recovered, and a sufficient amount of trimagnesium phosphate is added to the DCPD to provide additional hydrolytic stability. Then, at least 0.1 percent, based on the weight of the DCPD, of a pharmaceutically acceptable salt of a polyphosphate is added to provide the composition of the present invention.

DCPD containing the pyrophosphate complex can be prepared by any number of techniques known to those skilled in the art. Generally, a basic calcium-containing material, such as calcium carbonate, calcium oxide, calcium hydroxide and mixtures thereof, including mixtures commonly known as slaked lime, quick lime and hydrated lime, are added to dilute aqueous solutions of orthophosphoric acid to precipitate DCPD. Then, hydrolytic stability of the DCPD from the pyrophosphate complex is achieved by adding a calcium-/alkali metal pyrophosphate or a soluble pyrophosphate salt to the DCPD such as is disclosed in U.S. Pat. Nos. 2,287,699; 3,012,852; 3,169,096; 3,411,873 and the like.

In the preferred embodiment, the DCPD is prepared by adding 0.3 weight percent $P_2O_5$ as pyrophosphate or tetraalkali metal pyrophosphate to an aqueous mixture containing DCPD having a pH from about 5.5 to about 6.5 and then adding a sufficient amount of lime to the DCPD slurry to provide a pH from about 6.5 to about 8.0.

The soluble pyrophosphate salts useful for preparing the pyrophosphate complex are well known to those skilled in the art. Tetrasodium pyrophosphate and tetrapotassium pyrophosphate are preferred and tetrasodium pyrophosphate is especially preferred to form the pyrophosphate complex. The amount of soluble pyrophosphate salt to be added to the DCPD to provide partial hydrolytic stability ranges from about 0.1 to about 5 percent by weight of $P_2O_5$, as pyrophosphate, based on the weight of the DCPD. It is preferred to add the soluble pyrophosphate salt in an amount corresponding to an addition of from about 0.5 to about 2.5 percent by weight of $P_2O_5$, as pyrophosphate, based on the weight of the DCPD. On yet another basis, the soluble pyrophosphate salt is added in an amount which results in a DCPD containing from about 0.2 to about 2.5 percent by weight of pyrophosphate $P_2O_5$, which would represent typical stabilized DCPD.

After the DCPD containing the pyrophosphate complex is recovered, dried and milled, it is then admixed with trimagnesium phosphate. The amount of trimagnesium phosphate that can be used in the composition of the present invention can vary within wide limits. The beneficial effects of the trimagnesium phosphate are generally not observed at concentrations less than about 0.1 weight percent, based on the weight of the DCPD and additional fluoride stability is not seen at concentrations above about 5 weight percent, based on the weight of the DCPD. It is preferred to add between about 0.5 weight percent and about 3 weight percent, based on the weight of the DCPD.

The trimagnesium phosphate used to prepare the composition of the present invention is generally added to the octahydrate. However, other hydrates of magnesium phosphate may be equivalent, since the exact form of the magnesium phosphate after it has been incorporated into a DCPD-based toothpaste formulation is not known. Hence, anhydrous trimagnesium phosphate or trimagnesium phosphates containing 8 to 22 waters of hydration, or even dimagnesium phosphate hydrates, are deemed to be equivalent for purposes of this invention, although the use of trimagnesium phosphate octahydrate is preferred.

There is also added to the DCPD from about 0.1 weight percent to about 3 weight percent, based on the weight of the DCPD, of at least one pharmaceutically acceptable polyphosphate salt. The pharmaceutically acceptable polyphosphate salt can be added to the DCPD by techniques known to the art such as by blending the powdered salt with the DCPD.

According to the present invention, the pharmaceutically acceptable polyphosphate salt and the trimagnesium phosphate can be added to the DCPD containing the pyrophosphate complex at any stage before the DCPD is incorporated into a toothpaste formulation. The order of addition is not believed to be important, but we prefer to add the trimagnesium phosphate to the DCPD before we add the pharmaceutically acceptable condensed phosphate salt.

Any number of pharmaceutically acceptable polyphosphate salts known to those skilled in the art can be used in the method of the present invention. Sodium and potassium salts, either singly or admixed together or with other elements such as calcium and the like, are generally considered to be pharmaceutically acceptable. Hence, suitable polyphosphate salts include the pharmaceutically acceptable salts of polyphosphates such as pentasodium tripolyphosphate, pentapotassium tripolyphosphate, and hydrogen containing sodium or potassium tripolyphosphates ($Na_4HP_3O_{10}$, $K_3H_2P_3O_{10}$) and the like. Pentasodium tripolyphosphate is preferred.

Pharmaceutically acceptable salts of orthophosphates, pyrophosphates, ultraphosphates, metaphosphates, phosphate glasses and the like do not provide the same degree of fluoride stability to the DCPD as the polyphosphates, and hence, are outside the scope of the present invention. However, the presence of pharmaceutically acceptable salts of these other phosphorus compounds is generally not harmful, and indeed, the presence of from about 0.1 to about 3 weight percent, preferably from about 0.3 to about 1 weight percent, based on the weight of the DCPD, of an alkali metal orthophosphate in combination with the polyphosphate salt is preferred.

The amount of the pharmaceutically acceptable polyphosphate salt can vary within wide limits. Although beneficial effects are observed at concentrations as low as about 0.1 percent, based on the weight of the DCPD, it is preferred to use higher concentrations, say greater than about 0.3 weight percent. There does not seem to be a beneficial effect in using more than about 3 weight percent, based on the weight of the DCPD, and the presence of higher concentrations of the polyphosphate salts may degrade hydrolytic stability to some degree. The exact concentration of the pharmaceutically acceptable polyphosphate salt will depend upon a number of factors, as will occur to those skilled in the art in view of the present disclosure, such as the amount of trimagnesium phosphate and the amount of the pyrophosphate complex, the grade of the DCPD, the particular polyphoshate salt used, and the like. However, it is preferred to provide concentrations between about 0.3 weight percent and about 2 weight percent, based on the weight of the DCPD.

The mechanism by which the pyrophosphate complex and the trimagnesium phosphate and the polyphosphates provide the superior hydrolytic stability to DCPD is not understood. At first it was believed that since the polyphosphates are known to be strong calcium sequestering agents that the superior results were achieved by this action. However, when a DCPD composition containing the pyrophosphate complex and trimagnesium complex was admixed with trisodium nitrilotriacetate or tetrasodium ethylenediamine tetraacetate to provide improved hydrolytic stability, the fluoride stability of the resulting DCPD was not as good as that obtained by using polyphosphates.

The DCPD of the present invention can be used in toothpaste formulations with alkali metal monofluorophosphates such as sodium monofluorophosphate, potassium monofluorophosphate and the like. Sodium monofluorophosphate is preferred for use with DCPD.

According to the present invention, the DCPD can also contain other dental polishing agents, as will occur to those skilled in the art. Such dental polishing agents include, but are not limited to, insoluble metaphosphates, silica gels, alumina, chalk and the like. Although satisfactory results are achieved using the DCPD of the present invention, it may be desirable to add an additional abrasive and polishing agent such as anhydrous dicalcium phosphate, i.e., precipitated anhydrous dicalcium phosphate, in order to clean teeth that are very heavily coated with discoloring material, food particles, tartar and the like. The preparation of such DCPD containing a minor amount of such additional polishing agents is known to those skilled in the art, such as described in U.S. Pat. No. 3,334,979.

In the formation of finished dentifrice compositions containing the composition of the present invention, practically any of the auxillary agents that are conventionally utilized in toothpastes and/or tooth powder formulations can be used in conjunction with the composition of the present invention. Toothpastes, for example, will generally contain: a source of fluoride ion, such as sodium monofluorophosphate; a sweetener, such as saccharin; a humectant, such as sorbitol or glycerine; a binding agent, such as hydroethyl cellulose, carboxymethyl cellulose, and the like; a sudsing agent, such as sodium lauryl sulfate, sucrose monolaurate or tridecyl alcohol that has been reacted with from about 3 to about 10 moles of ethylene oxide per mole of alcohol; and a flavoring agent.

In toothpastes, the level of the composition of the present invention that is utilized can generally be varied from about 20 to about 60 weight percent, and preferably from about 30 to about 45 weight percent of the formulation. As noted above, the composition of the present invention need not be the only abrasive in the dentifrice formulation, although it is generally preferred that the composition of the present invention represents at least about half of all of the abrasive materials in the dentifrice formulation. In tooth powders, higher amounts of the composition of the present invention can be used, say up to about 95 weight percent.

DESCRIPTION OF THE PREFERRED EMBODIMENTS

This invention is illustrated by, but not limited to, the following Examples wherein all percentages are by weight unless otherwise indicated.

EXAMPLE I

An aqueous slurry containing DCPD is prepared by the reaction of phosphoric acid and lime in an aqueous media. The resulting slurry contains approximately 30 percent DCPD and the slurry pH is 5.8.

A 2780 gram sample of the DCPD aqueous slurry with pH adjusted to 6.5 using lime slurry (13.5 percent CaO) is charged to a one gallon reactor equipped with stirrer. There is added to this slurry 188 grams of a 9 percent tetrasodium pyrophosphate aqueous solution (2 percent TSPP based on the DCPD present) and the mixture is stirred for 45 minutes at about 29° C. The pH is then adjusted to about 7.7 with aqueous lime slurry (13.5 percent CaO) and the solid DCPD product is separated from the slurry, dried and milled. A small portion of the sample was separated and the $P_2O_5$ levels corresponding to the pyrophosphate complex present is determined substantially in accordance with the well known ion exchange method for analysis of sodium triphosphate [ASTM D-2671-70 (reapproved 1975), entitled "Standard Method for Analysis of Sodium Triphosphate by the Simplified Ion Exchange Method"]. The pyrophosphate complex content is found to be about 0.5 percent.

Portions of the above DCPD containing the pyrophosphate complex are blended with powdered trimagnesium phosphate and/or powdered phosphates, and used to prepare a toothpaste formulation similar to that disclosed in U.S. Pat. No. 3,308,029 issued Mar. 7, 1967 which is typical to those that are commercially available, except for flavor. It contains about 1,000 ppm added fluoride. The formulation is set forth below:

|  | Parts by Weight |
|---|---|
| Glycerine | 21.8 |
| DCPD | 49.6 |
| Sodium Lauryl Sulfate | 1.5 |
| Saccharin | 0.2 |
| Water | 25.2 |
| Sodium Monofluorophosphate | 0.8 |
| Carboxymethyl Cellulose | 0.9 |
|  | 100.0 |

Samples of the above paste are transferred to plastic bottles. Thereafter, the plastic bottles are stoppered and placed in an oven at 50° C. for six weeks as an accelerated test to simulate two years storage. After the six weeks storage, the bottles are removed from the oven and the fluoride ion concentration of the formulation is measured potentiometrically. The results of the storage after six weeks are shown in Table 1.

TABLE 1

| | DCPD STABILITY | | |
|---|---|---|---|
| | Powdered Additive to DCPD[a] | | SOLUBLE F REMAINING |
| Sample | Identity | Wt. % | (ppm) |
| 1 | — | — | 190 |
| 2 | Sodium Tripolyphosphate | 1 | 290 |
| 3 | Trimagnesium Phosphate | 2 | 390 |
| 4 | Trimagnesium Phosphate | 3 | 390 |
| 5 | Trimagnesium Phosphate<br>Glassy Sodium Polyphosphate[b] | 2<br>1 | 430 |
| 6 | Trimagnesium Phosphate<br>Sodium Hexametaphosphate | 2<br>1 | 455 |
| 7 | Trimagnesium Phosphate<br>Sodium Trimetaphosphate | 2<br>1 | 490 |
| 8 | Trimagnesium Phosphate<br>SQ Glassy Phosphate[c] | 2<br>1 | 490 |
| 9 | Trimagnesium Phosphate<br>Tetrasodium Pyrophosphate | 2<br>1 | 495 |
| 10 | Trimagnesium Phosphate<br>Pentasodium Tripolyphosphate | 2<br>1 | 565 |

[a]DCPD containing 0.5 percent pyrophosphate complex
[b]containing about 200 phosphorus atoms
[c]available commercially from Monsanto Company, St. Louis, Missouri.

Thus, it can be seen that Sample 10, a composition falling within the scope of the present invention, has superior hydrolytic stability over other systems, as evidenced by the superior fluoride stability.

EXAMPLE II

The procedure of Example I is repeated. The added fluoride content of the toothpaste formulation is about 1,000 ppm. The results are shown in Table 2.

TABLE 2

| | DCPD STABILITY | | |
|---|---|---|---|
| | Powdered Additive to DCPD | | Soluble F |
| Sample | Identity | Wt. % | Remaining (ppm) |
| 11 | — | — | 190 |
| 12 | Trimagnesium Phosphate | 2 | 510 |
| 13 | Trimagnesium Phosphate | 5 | 480 |
| 14 | Pentasodium Tripolyphosphate<br>Sodium Metaphosphate | 0.5<br>0.5 | 330 |
| 15 | Pentasodium Tripolyphosphate<br>Disodium Dihydrogen Pyrophosphate | 0.5<br>0.5 | 290 |
| 16 | Trimagnesium Phosphate<br>Pentasodium Tripolyphosphate | 2<br>2 | 570 |
| 17 | Trimagnesium Phosphate<br>Pentasodium Tripolyphosphate | 2<br>1.5 | 550 |
| 18 | Trimagnesium Phosphate<br>Pentasodium Tripolyphosphate | 2<br>1 | 570 |
| 19 | Trimagnesium Phosphate<br>Pentasodium Tripolyphosphate<br>Sodium Hexametaphosphate | 2<br>0.5<br>0.5 | 600 |
| 20 | Trimagnesium Phosphate<br>Pentasodium Tripolyphosphate<br>Disodium Dihydrogen Pyrophosphate | 2<br>0.5<br>0.5 | 590 |

EXAMPLE III

A sample of the DCPD from Example II is blended with 2 percent trimagnesium phosphate, 1 percent pentasodium tripolyphosphate and 0.05 percent monosodium phosphate. When the DCPD is used in the toothpaste formulation of Example II containing about 1,000 ppm added fluoride and stored for 6 weeks at 50° C., about 610 ppm soluble fluoride remains after the test.

Thus, it can be seen from Samples 16 through 20 in Example II, and from Example III, that superior soluble fluoride stability is achieved by the DCPD composition of the present invention.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A composition which comprises dicalcium phosphate dihydrate and (a) from about 0.1 weight percent to about 5 weight percent $P_2O_5$ equivalent of pyrophosphate complex; (b) from about 0.1 weight percent to about 5 weight percent trimagnesium phosphate; and (c) from about 0.1 weight percent to about 3 weight percent of a pharmaceutically acceptable polyphosphate salt; based on the weight of the dicalcium phosphate dihydrate.

2. A composition of claim 1 wherein the amount of pyrophosphate complex is from about 0.5 weight percent to about 2.5 weight percent $P_2O_5$ equivalent.

3. A composition of claim 1 wherein the amount of trimagnesium phosphate is from about 0.5 weight percent to about 2.5 weight percent.

4. A composition of claim 1 wherein the amount of the pharmaceutically acceptable polyphosphate salt is from about 0.3 weight percent to about 2 weight percent.

5. A composition of claim 4 wherein the amount of pyrophosphate complex is from about 0.5 weight percent to about 2.5 weight percent $P_2O_5$ equivalent, and the amount of trimagnesium phosphate is from about 0.5 weight percent to about 2.5 weight percent.

6. A composition of claim 5 wherein the pharmaceutically acceptable polyphosphate is pentasodium tripolyphosphate.

7. A composition of claim 5 or 6 wherein there is added to the composition from about 0.1 weight percent to about 3 weight percent, based on the weight of the dicalcium phosphate dihydrate, of an alkali metal orthophosphate.

8. A composition of claim 5 or 6 wherein there is added to the composition from about 0.3 weight percent to about 1 weight percent, based on the weight of the dicalcium phosphate dihydrate, of an alkali metal orthophosphate.

9. A composition of claim 6 wherein there is added to the composition from about 0.3 weight percent to about 1 weight percent, based on the weight of the dicalcium phosphate dihydrate, of monosodium dihydrogen phosphate.

* * * * *